(12) United States Patent
Van Voris et al.

(10) Patent No.: US 6,331,308 B1
(45) Date of Patent: *Dec. 18, 2001

(54) METHOD AND APPARATUS FOR PROVIDING LONG TERM PROTECTION FROM INTRUSION BY INSECTS AND OTHER COLD BLOODED ANIMALS

(75) Inventors: Peter Van Voris, Richland; Dominic A. Cataldo, Kennewick, both of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/342,529

(22) Filed: Jun. 29, 1999

Related U.S. Application Data

(63) Continuation of application No. 08/482,300, filed on Jun. 7, 1995, now Pat. No. 6,060,076, which is a continuation-in-part of application No. 08/348,774, filed on Dec. 1, 1994, now abandoned, which is a continuation of application No. 08/117,877, filed on Sep. 7, 1993, now abandoned, which is a continuation of application No. 07/893,970, filed on Jun. 4, 1992, now abandoned, which is a continuation of application No. 07/401,955, filed on Sep. 1, 1989, now abandoned, which is a continuation-in-part of application No. 07/555,113, filed on Jul. 19, 1990, now Pat. No. 4,998,959, which is a continuation-in-part of application No. 06/314,809, filed on Oct. 26, 1981, now abandoned, which is a continuation-in-part of application No. 06/314,810, filed on Oct. 26, 1981, now abandoned.

(51) Int. Cl.⁷ .......................... A01N 25/10; A01N 25/34; A01N 37/12; A01N 47/40
(52) U.S. Cl. .......................... 424/411; 514/521; 514/531; 514/723.3; 514/953
(58) Field of Search .......................... 424/411; 514/521, 514/531, 723.3, 953

(56) References Cited

U.S. PATENT DOCUMENTS

| | | | |
|---|---|---|---|
| Re. 32,356 | 2/1987 | Cardarelli | 424/78 |
| 1,999,458 | 4/1935 | Hollister | 47/1 |
| 2,269,626 | 1/1942 | Henry | 156/20 |
| 2,970,404 | 2/1961 | Beaufils et al. | 47/57.5 |
| 3,111,403 | 11/1963 | Soper | 71/2.3 |
| 3,231,398 | 1/1966 | Pauli | 106/16 |
| 3,235,366 | 2/1966 | Seymour et al. | 71/2.6 |
| 3,257,190 | 6/1966 | Soper | 71/2.3 |
| 3,367,065 | 2/1968 | Cravens | 47/57.3 |
| 3,384,993 | 5/1968 | Kane | 47/58 |
| 3,502,458 | 3/1970 | Schenk | 71/64 |
| 3,551,192 | 12/1970 | Reinert | 117/138.8 |
| 3,592,792 | 7/1971 | Newland et al. | 260/41 |
| 3,608,062 | 9/1971 | Alfes et al. | 424/22 |
| 3,639,583 * | 2/1972 | Cardarelli et al. | 424/125 |
| 3,671,548 | 6/1972 | Itaya et al. | 549/79 |
| 3,691,683 | 9/1972 | Sterzik | 47/57.5 |
| 3,697,253 | 10/1972 | MacMurray | 71/97 |
| 3,705,938 | 12/1972 | Hyman et al. | 424/19 |
| 3,706,161 | 12/1972 | Jenson | 47/57.5 |
| 3,716,560 | 2/1973 | Taya et al. | 549/471 |
| 3,740,419 | 6/1973 | Campbell | 424/409 |
| 3,741,807 | 6/1973 | Horne | 134/24 |
| 3,759,941 | 9/1973 | Sampei et al. | 549/117 |

(List continued on next page.)

FOREIGN PATENT DOCUMENTS

| | | |
|---|---|---|
| A 16980/83 | 7/1983 | (AU) . |
| B-23427/84 | 8/1984 | (AU) . |
| A 48655/90 | 8/1990 | (AU) . |
| A 62329/90 | 3/1991 | (AU) . |
| 62329/90 A * | 3/1991 | (AU) . |
| B-82443/91 | 2/1992 | (AU) . |
| B-13886/95 | 8/1995 | (AU) . |
| A 52454/96 | 12/1996 | (AU) . |
| 2 070 231 A1 | 12/1992 | (CA) . |
| 1 929 314 * | 6/1969 | (DE) . |
| 0 152 976 * | 8/1985 | (EP) . |
| 0 286 009 A2 | 10/1988 | (EP) . |
| 0 594 892 A1 | 5/1994 | (EP) . |
| 2 018 593 A | 10/1979 | (GB) . |
| 2 098 541 A | 11/1982 | (GB) . |
| 52-72802 | 6/1977 | (JP) . |
| 58 39601 | 3/1983 | (JP) . |
| 5811 3102 | 7/1983 | (JP) . |
| 602 02801 A | 10/1985 | (JP) . |
| 62-236937 | 10/1987 | (JP) . |
| 64-58739A | 3/1989 | (JP) . |
| 8302080 A | 11/1996 | (JP) . |
| 1690654 | 11/1991 | (SU) . |
| WO 84/02447 | 7/1984 | (WO) . |
| WO 90/14004 | 11/1990 | (WO) . |
| WO 92/03927 | 3/1992 | (WO) . |
| WO 95/18532 | 7/1995 | (WO) . |
| WO 97/47190 | 12/1997 | (WO) . |
| WO 98/21960 | 5/1998 | (WO) . |
| 86/1133 | 2/1986 | (ZA) . |

OTHER PUBLICATIONS

Kemi Horutsu KK. Intellectual Property Network abstract of JP 6–294165 A2. Oct. 1994.*

Nihon Tokushu Noyaku Seizo KK. WPI/Derwent abstract 85–293614 of JP 60–020801 A. Oct. 1985.*

(List continued on next page.)

*Primary Examiner*—S. Mark Clardy
(74) *Attorney, Agent, or Firm*—Jenkens & Gilchrist

(57) ABSTRACT

Controlled release devices are shaped and placed in locations through which insects and/or other cold blooded animals generally enter an area or a structure sought to be protected. The controlled release devices include a polymeric matrix and a pesticide contained in the matrix. The pesticide is gradually released out of the matrix to the surface of the device. The pesticide on the surface of the device kills the intruding insects or other cold blooded animals that come in contact with the pesticide. In addition, if the device is in contact with a permeable structure or object, the pesticide released onto the surface of the device is absorbed by such permeable structure or object to provide a barrier to entry by the insects and/or other cold blooded animals.

70 Claims, No Drawings

U.S. PATENT DOCUMENTS

| | | | |
|---|---|---|---|
| 3,835,176 | 9/1974 | Matsuo et al. | 558/407 |
| 3,835,220 | 9/1974 | Matsui et al. | 424/40 |
| 3,846,500 | 11/1974 | Kitamura et al. | 568/660 |
| 3,851,053 | 11/1974 | Cardarelli | 424/78 |
| 3,857,934 | 12/1974 | Bernstein et al. | 424/30 |
| 3,864,114 | 2/1975 | Green | 71/3 |
| 3,864,388 | 2/1975 | Kitamura et al. | 560/60 |
| 3,867,542 | 2/1975 | Ueda et al. | 514/461 |
| 3,876,681 | 4/1975 | Okuno et al. | 560/124 |
| 3,880,643 | 4/1975 | Cooke et al. | 71/78 |
| 3,891,423 | 6/1975 | Stanley et al. | 71/86 |
| 3,899,586 | 8/1975 | Okuno et al. | 514/417 |
| 3,906,089 | 9/1975 | Okuno et al. | 424/45 |
| 3,939,606 | 2/1976 | Vandemark et al. | 47/9 |
| 3,954,814 | 5/1976 | Mizutani et al. | 549/449 |
| 3,966,963 | 6/1976 | Okuno et al. | 514/531 |
| 3,970,703 | 7/1976 | Kitamura et al. | 568/662 |
| 3,981,903 | 9/1976 | Hirano et al. | 560/124 |
| 3,998,868 | 12/1976 | Mitzutani et al. | 560/124 |
| 4,003,945 | 1/1977 | Kitamura et al. | 560/124 |
| 4,007,258 | 2/1977 | Cohen et al. | 424/22 |
| 4,021,122 | 5/1977 | Krenmayr | 356/240 |
| 4,037,352 | 7/1977 | Hennart et al. | 43/129 |
| 4,063,919 | 12/1977 | Grano, Jr. | 71/11 |
| 4,065,555 | 12/1977 | Potter | 424/83 |
| 4,066,441 | 1/1978 | Lutz et al. | 71/121 |
| 4,077,795 | 3/1978 | Cooke et al. | 71/78 |
| 4,082,533 | 4/1978 | Wittenbrook et al. | 71/28 |
| 4,101,582 | 7/1978 | Lutz et al. | 260/574 |
| 4,102,991 | 7/1978 | Kydonieus | 424/27 |
| 4,104,374 | 8/1978 | Reuther et al. | 424/185 |
| 4,118,505 | 10/1978 | Kitamura et al. | 514/438 |
| 4,123,250 | 10/1978 | Kupelian | 71/78 |
| 4,160,335 | 7/1979 | Von Kohorn et al. | 43/131 |
| 4,172,904 | 10/1979 | Young et al. | 427/4 |
| 4,176,189 | 11/1979 | Itaya et al. | 514/389 |
| 4,190,680 | 2/1980 | Young et al. | 427/4 |
| 4,193,984 | 3/1980 | Kydonieus | 424/16 |
| 4,198,441 | 4/1980 | Young et al. | 427/2 |
| 4,198,782 | 4/1980 | Kydonieus et al. | 47/58 |
| 4,200,664 | 4/1980 | Young et al. | 427/4 |
| 4,205,096 | 5/1980 | Young et al. | 427/4 |
| 4,212,879 | 7/1980 | Ohsumi et al. | 514/427 |
| 4,229,469 | 10/1980 | Mizutani et al. | 514/519 |
| 4,235,872 | 11/1980 | Tocker | 424/19 |
| 4,237,113 | 12/1980 | Cardarelli | 424/78 |
| 4,237,114 | 12/1980 | Cardarelli | 424/78 |
| 4,243,703 | 1/1981 | Palvarini et al. | 427/276 |
| 4,260,626 | 4/1981 | Carr et al. | 424/276 R |
| 4,263,463 | 4/1981 | Kitamura et al. | 568/873 |
| 4,269,626 | 5/1981 | Gorke et al. | 106/18.32 |
| 4,272,520 | 6/1981 | Kydonieus et al. | 424/84 |
| 4,279,924 | 7/1981 | Suzuki et al. | 514/521 |
| 4,282,207 | 8/1981 | Young et al. | 424/78 |
| 4,282,209 | 8/1981 | Tocker | 424/81 |
| 4,293,504 | 10/1981 | Suzuki et al. | 558/354 |
| 4,320,113 * | 3/1982 | Kydonieus | 424/27 |
| 4,327,109 | 4/1982 | Mizutani et al. | 514/443 |
| 4,336,194 | 6/1982 | Ohsumi et al. | 548/562 |
| 4,344,250 | 8/1982 | Fahlstrom | 47/57.5 |
| 4,348,218 | 9/1982 | Bond, Jr. | 71/1 |
| 4,350,678 | 9/1982 | Palvarini et al. | 424/27 |
| 4,352,833 | 10/1982 | Young et al. | 427/4 |
| 4,360,376 | 11/1982 | Koestler | 71/121 |
| 4,374,126 | 2/1983 | Cardarelli et al. | 424/81 |
| 4,376,785 | 3/1983 | Matsuo et al. | 514/521 |
| 4,377,675 | 3/1983 | Daudt et al. | 528/25 |
| 4,400,374 | 8/1983 | Cardarelli | 424/78 |
| 4,405,360 | 9/1983 | Cardarelli | 71/117 |
| 4,435,383 | 3/1984 | Wysong | 424/78 |
| 4,457,929 | 7/1984 | Kamachi et al. | 424/246 |
| 4,496,586 | 1/1985 | Matsui et al. | 514/531 |
| 4,500,337 | 2/1985 | Young et al. | 71/67 |
| 4,500,338 | 2/1985 | Young et al. | 71/67 |
| 4,500,339 | 2/1985 | Young et al. | 71/67 |
| 4,503,071 | 3/1985 | Hirano et al. | 514/521 |
| 4,508,568 | 4/1985 | Fox | 106/2 |
| 4,576,801 | 3/1986 | Parry et al. | 427/288 |
| 4,579,085 * | 4/1986 | McGuire | 119/156 |
| 4,639,393 | 1/1987 | Von Kohorn et al. | 428/304.4 |
| 4,666,706 | 5/1987 | Farquharson et al. | 424/408 |
| 4,666,767 | 5/1987 | Von Kohorn et al. | 428/304.4 |
| 4,680,328 | 7/1987 | Dohrer et al. | 524/137 |
| 4,747,902 | 5/1988 | Saitoh | 156/244.11 |
| 4,767,812 | 8/1988 | Chapin et al. | 524/144 |
| 4,808,454 | 2/1989 | Saitoh | 428/40.6 |
| 4,818,525 | 4/1989 | Kamada et al. | 424/81 |
| 4,842,860 * | 6/1989 | Sugiura et al. | 424/403 |
| 4,886,656 | 12/1989 | Obayashi et al. | 514/144 |
| 4,921,703 | 5/1990 | Higuchi et al. | 424/419 |
| 4,929,497 | 5/1990 | Mitchell et al. | 428/265 |
| 4,971,796 | 11/1990 | Sjogren | 424/417 |
| 5,019,998 | 5/1991 | Cowen et al. | 364/496 |
| 5,083,408 | 1/1992 | Blom et al. | 52/57 |
| 5,104,659 | 4/1992 | Fishbein et al. | 424/411 |
| 5,116,414 | 5/1992 | Burton et al. | 71/121 |
| 5,135,744 * | 8/1992 | Alexander et al. | 424/409 |
| 5,139,566 | 8/1992 | Zimmerman | 71/121 |
| 5,181,952 | 1/1993 | Burton et al. | 504/347 |
| 5,201,925 | 4/1993 | Itzel et al. | 47/58 |
| 5,292,504 | 3/1994 | Cardin et al. | 514/65 |
| 5,296,227 | 3/1994 | Norval et al. | 424/411 |
| 5,317,834 | 6/1994 | Anderson | 47/48.5 |
| 5,439,924 | 8/1995 | Mills | 514/345 |
| 5,449,250 | 9/1995 | Burton et al. | 405/128 |
| 5,492,696 | 2/1996 | Price et al. | 424/417 |
| 5,525,147 | 6/1996 | Dunstan et al. | 106/18.3 |
| 5,801,194 | 9/1998 | Voris et al. | 514/531 |
| 5,856,271 | 1/1999 | Cataldo et al. | 504/116 |
| 5,860,266 | 1/1999 | Martinet et al. | 52/741.3 |
| 5,898,019 | 4/1999 | Van Voris et al. | 504/116 |
| 5,925,368 | 7/1999 | Voris et al. | 424/405 |
| 6,060,076 | 5/2000 | Voris et al. | 424/411 |
| 6,099,850 | 8/2000 | Voris et al. | 424/411 |

OTHER PUBLICATIONS

Baker and Lonsdale, "Controlled Delivery—an emerging use for membranes", Chemtech, Nov. 1975, pp. 668–674.

Burton et al., "Application of Controlled Release Technology to Uranium Mill Tailings Stabilization", presented at American Nuclear Society Topical Meeting on Waste Management, Feb. 23–26, 1981, Tucson, Arizona, pp. 1009–1021.

Burton et al., "A Controlled–Release Herbicide Device For Multiple–Year Control of Roots at Waste Burial Sites", $10^{th}$ International Symposium on Controlled Release of Bioactive Materials, Jul. 24–27, 1983, San Francisco, California, pp. 305–308.

Burton et al., "The Use of Controlled Release Herbicides in Waste Burial Sites", presented at the Eigth International Controlled Release Symposium, Fort Lauderdale, Florida, Jul. 26–29, 1981.** A Copy of this Reference is not available.

PNL–3000–6 Nuclear Waste Management Quarterly Progress Report, Apr. through Jun. 1980. Sep. 1980. Prepared for the U.S. Department of Energy under Contract DE–AC06–76RLO 1830, pp. 22.1 and 22.1, "Application of Long–Term Chemical Biobarriers for Uranium Tailings".** A Copy of this Reference is not available.

Kumar, et al., "The effect . . . treated wood," *J. Timber Dev . . . India* (1977), 23(3), pp. 9–13.** A Copy of this Reference is not available.

French Pat. 2,358,831. Chem. Abst. vol. 89, (1978), 158777f. Index Citation.** A Copy of this Reference is not available.

The Agrochemical.s Handbook, $2^{nd}$ Ed., D. Hartley, ed. The Royal. Society of Chemistry (1987).** A Copy of this Reference is not available.

The Pesticide Manual., $8^{th}$ Ed., C. Worthington, Ed., British Crop Protection Council, 1987, pp. 7179–7180.** A Copy of this Reference is not available.

Offenlegunsschrift 1929314; Chem. Abstracts vol. 88 entry 75 506 V. **A Copy of this Reference is not available.

Morrell, J., Woodpole Conference Proceedings, 03/10–11/86.** A copy of this reference not available.

Hayes, W.C., Extending Woodpole Life: Solving a $5 Billion Dollar a Year Program, Electrical World, p. 41–47, Feb. 1986.

Shepherd, M., Managing America's Wood Pole Inventory, EPRI Journal., Sep. 1987, vol. 12, No. 6.

Zable, R. et al. The Fungal. Associates, Detection, and Fumigant Control of Decay in Treated Southern Pine Poles, Final. Report EL–27GA for EPRI Research Project 47191, State University of New York, 1982.** A Copy of this Reference is not available.

Graham et al. Controlling Biological. Deterioration of Wood with Volatile Chemicals, EPRI Report EL–1480 (Oregon State Unversity) 1980.** A Copy of this Reference is not available.

Boron as a Preservative Against Internal Decay, Dickinson, Morris, Calver, Distrib. Dev., Mar. 1989, v 89:1, p 9–14.** A Copy of this Reference is not available.

Gelatin Encapsulation of Methylisothiocyanate for Control of Wood–Decay Fungi, Zahora, Corden, Forest Products Journal, vol. 35 (7/8): pp: 64–69, 1985.** A Copy of this Reference is not available.

Groundline Repair for Wood Poles, EPRI Journal, Apr./May 1986.** A Copy of this Reference is not available.

N. N. Mel'nikov, Chemistry and Technology of Pesticide, Moscow, Khimiya, 1974, pp. 26–30 date unknown (translation).

A. Pajak et al., "Morphological and Cytological Effects Brought About By Trifluralin on Pea (Pisum Sativum L.)", *Biuletyn Warzywniczy*, pp. 451–462, 1979, (abstract provided as first page).

Y. Eshel et al., "Effect of Dinitroanilines on Solanaceous Vegetables and Soil Fungi", *Weed Science*, pp. 243–246, vol. 20, Issue 3, May 1972.

Burton, et al., "A Controlled–Release Herbicide Device for Multiple–Year Control of Roots at Waste Burial. Sites," *Journal of Controlled Release* (1985), 8 pages.

Chang, et al.., "Control of Ant Damage to Polyethylene Tubes Used in Drip Irrigation Systems in Hawaiian Sugarcane Fields," *International. Society of Sugar Cane Technologies* (Feb./1–11/80), pp. 1686–1692.

Chen, et al., "Approaches to the Improvement of Biological Resistance of Wood through Controlled Release Technology," *Proceedings of the 13th Int't Symposium on Controlled Release of Bioactive Material.s* (Aug./3–6/1986), pp. 75–76.

Batelle Technology Transfer Bulletin, "Controlled–Release Chemical.s for Inhibiting Plant Roots," 2 pp. (12/84).

Cline et al., "Biobarriers used in Shallow Burial. Ground Stabilization," *Nuclear Technology*, vol. 58, pp. 150–153 (1982).

Hughes, "Controlled Release Technology Inhibits Root Growth," *Controlled Release Business and Technology*, 1989, p. 15.

Jury et al., "Behaviour Assessment Model for Trace Organics in Soil: I. Model Description," *J. Environ. Qual.*, vol. 12, No. 4, pp. 558–564, (1983).

Jury et al., "Behaviour Assessment Model for Trace Organics in Soil: III Application of Screening Model," *J. Environ. Qual.*, vol. 13, No. 4, pp. 573–579, (1984).

Jury et al., "Behaviour Assessment Model for Trace Organics in Soil: IV. Review of Experimental. Evidence," *J.Environ. Qual.*, vol. 13, No. 4, pp. 580–586, (1984).

Roseman et al., "Chapter 18: The Use of Controlled Release Herbicides in Waste Burial. Sites," Controlled Release Delivery Systems Marcel Dekker, NY, (1983).

"Soil Fumigants are Remarkably Effective in Stopping Decay of Wood," *Chemical. Week*, p. 39, (Sep. 25, 1974). *Abstract.

Solie et al., "Simulation of Triflural in Diffusion in the Soil," *Transactions of the ASAE*, pp. 1463–1467, (1984).

Steyaart, "Proceedings, Eighty–Second Annual Meeting of the American Wood–Preservers' Association: Address," *Crossties*, vol. 68, No. 3, pp. 45–46, Mar. 1987.

Streile, "The Effect of Temperature on Pesticide Phase Partitioning, Trasnport, and Volatilization from Soil," *Abstract of the Dissertation*, (1984), 37 pages.

Van Voris et al., "Long–Term Controlled Release of Herbicides: Root–Growth–Inhibiting Biobarrier Technology," pp. 1–19, No Date.

Probst et al., "Fate of Trifluralin in Soils and Plants", J. Agric. Food Chem., vol. 15, No. 4, Jul.–Aug. 1967, pp. 592–599.

Delcourt et al., Chem. Abst., Cytologia, vol. 41, No. 1, Jan. 1976, pp. 75–84.

Lignowski et al., "Trifluralin and Root Growth", Chem. Abst., Plant and Cell Physiology, vol. 76 (1972), pp. 701–708.

Chemical Abstracts, 88, 1978: 154553m, p. 1177.

* cited by examiner

METHOD AND APPARATUS FOR PROVIDING LONG TERM PROTECTION FROM INTRUSION BY INSECTS AND OTHER COLD BLOODED ANIMALS

CROSS REFERENCE TO RELATED APPLICATIONS

This application is a continuation of U.S. patent application Ser. No. 08/482,300 filed Jun. 7, 1995, which issued as U.S. Pat. No. 6,060,076; which is a continuation-in-part of U.S. patent application Ser. No. 08/348,774 filed Dec. 1, 1994, abandoned; which is a continuation of U.S. patent application Ser. No. 08/117,877 filed Sep. 7, 1993 abandoned; which is a continuation of U.S. patent application Ser. No. 07/893,970 filed Jun. 4, 1992 abandoned; which is a continuation of U.S. patent application Ser. No. 07/401,955 filed Sep. 1, 1989 abandoned.

BACKGROUND OF THE INVENTION

This invention relates to methods and devices for preventing insects and other cold blooded animals from intruding into certain areas or certain structures. In particular, it relates to providing long term protection against such intrusions.

Insects and other cold blooded animals need to be kept out certain areas and/or certain structures. Their intrusions into such areas or structures can create problems ranging in severity from merely a nuisance to those having dire consequences. For example, fire ants have to be kept out of electrical power distribution enclosures. Their intrusion into such enclosures can cause damage or even destruction of the electrical power distribution system. Fire ants also create a nuisance or damage by entering into buildings through cracks in the walls. In addition, the existence of fire ants in a quarantine zone can cause considerable expense to the plant nurseries in such zone. The plants which are shipped outside the zone must be certified to be ant free. The procedures used to assure that potted plants do not contain fire ants are relatively expensive and time consuming.

Similarly, intrusions by spiders of houses often produce unsightly webs which may be difficult to reach and eliminate.

In some areas, cold blooded animal other than insects create problems. For example, the brown tree snake, a venomous constrictor is a problem in the Pacific Islands, such as Guam and Hawaii where they frequently invade homes in search of food. Their control has been limited because of the collateral impact any effective control, would have on the endangered species.

Finally, crawling insects and soil borne insects can destroy crops and can create a nuisance and damage living areas.

SUMMARY OF THE INVENTION

Controlled release devices are shaped and placed in locations through which insects and/or other cold blooded animals generally enter an area or a structure sought to be protected. For the devices to be effective the release rate of the pesticide must be at least 10 $\mu g/cm^2$/day for insects and must be at least 40 $\mu g/cm^2$/day for cold blooded vertebrae animals. The controlled release devices include a polymeric matrix and a pesticide contained in the matrix. The pesticide is gradually released out of the matrix to the surface of the device. The pesticide on the surface of the device kills the intruding insects or other cold blooded animals that come into contact with the pesticide. In addition, if the device is in contact with a permeable structure or object, the pesticide released onto the surface of the device is absorbed by such permeable structure or object to provide a barrier to entry by the insects and/or other cold blooded animals. The pesticides that have been found useful in connection with the present invention include pyrethrins and fenoxycarb. The polymeric matrices can be made from any polymer which provides desired release rates and incorporates the pesticide without effecting its pesticidal activity. The preferred polymers include silicones, EVA, urethanes, polyurethanes, acrylonitrile butadene, acrylic rubber, ois isoprene and styrene-vinyl rubber.

The present invention is particularly useful in preventing intrusions by fire ants, spiders, crawling insects and other cold blooded animals such as snakes and lizards.

DETAILED DESCRIPTION

It has been discovered that controlled release devices which gradually release pesticides can be constructed to prevent, for a prolonged period of time, intrusions by insects and/or other cold blooded animals into areas, structures or objects that are sought to be protected from intrusions. The protection offered by the controlled release devices constructed and used in accordance with the present invention generally lasts from about 6 months to about 5 years.

Any polymer which can provide the desired release rate and which does not destroy the pesticidal nature of the pesticide used in the device can be employed to provide a polymeric in accordance with the present invention. Generally, suitable polymers can include both thermoset and thermoplastic polymers. Currently preferred polymers are silicones, urethanes, polyurethanes, acrylonitrile butadiene, acrylic rubber, styrene-vinyl rubber EVA and polyethylenes. Especially preferred are the following polymers: RTV-41, Hytrel, Solithane, Nipol 1312, Nipol 1312 LV, Hycar X16, Kraton D1101, Ultra Clear, Aromatic 80A urethane, Pellethane 2102-80A, Pellethane 2102-55D Alipmtic PS-49-100, Polyurethane 3100, Polyurethane 2200, EVA 763, Polyethylene MA 7800, and Polyethylene MA 78000.

Pesticides that can be employed in the matrices of the present invention include those that provide desired release rates at least about 10 $\mu g/cm^2$/day for insects and at least about 40 $\mu g/cm2$/day for cold blooded vertebras can be incorporated into a polymeric matrix and whose matricidal quality is not destroyed by incorporation in the matrix. The concentration of the pesticide in the matrix is generally in the range from about 2 to about 15 percent of the total weight of he matrix and preferably in the range from about 5 to about 10 percent.

In some control release devices of the present invention a carrier can be included to produce a desired release rate. A carrier can be carbon black clay or amorphous silica. Carbon black is currently preferred. The concentration of the carrier can range from about 2 to about 5 percent per total weight of the matrix, preferably it is in the range from about 3 to about 5 percent.

A description of general principles of making controlled release devices is given in U.S. patent application Ser. Nos. 06/555,113 filed Nov. 23, 1983 which is a continuation in part of Ser. Nos. 06/314,809 and 06/314,810 both filed on Oct. 26, 1981; Ser. No. 07/086,757, filed Aug. 18, 1987, Ser. No. 07/072,080 filed Jul. 10, 1987; and Ser. No. 07/091,918 filed Sep. 1, 1987. Methods for obtaining the release rates are described in patent application Ser. No. 07/303,707 filed on Jan. 30, 1989. The contents of these applications are being incorporated herein by reference.

The protection against intrusion is provided by the present invention as the result of the accumulation of the pesticide on the surface of the polymer matrix and/or the accumulation of the pesticide in an absorbent medium in contact with or in close proximity to the matrix, when the insect or other cold blooded animal comes in contact with pesticide it is repelled by it and/or killed by it. In case of insects, the pesticide is generally transferred to the feet of the insects and when the release rate of the pesticide is at least about 10 µg/cm2/day, sufficient amount of pesticide adheres to insect to kill it. It has been discovered that faster release rates are necessary for larger cold blooded animals. For snakes, and other cold blooded vertebrae animals, the pesticide release rates must be at least 40 µg/cm2/day.

EXAMPLE

The following controlled release devices were made and tested to obtain their release rates. The devices were made as follows. All devices, except for those employing S-113 urethane, were injection molded into a thin sheet about 1/8 inch thick. The device employing S-113 urethane was cast, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 87 to 83 percent by weight of polymer. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a 1/8 inch thick sheet and heated at about 60° C. for about 40 to 60 minutes to cure the cast sheet.

On inch squares were then cut from the thin sheets that were injection molded or cast and the squares were tested for release rates. The following release rates were obtained:

| Pesticide | Polymer | Release Rate |
| --- | --- | --- |
| Deltamethrin | S-113 urethane | 25.2 µg/cm$^2$/day |
| | Aromatic 80A | 16.8 µg/cm$^2$/day |
| | pellethane 2102-80A | 8.8 µg/cm$^2$/day |
| | pellethane 2102-55D | 8.0 µg/cm$^2$/day |
| | Alipmtic PS-49-100 | 7.2 µg/cm$^2$/day |
| Cypermethrin | polyurethane 3100 | 0.4 µg/cm$^2$/day |
| | polyurethane 2200 | 0.7 µg/cm$^2$/day |
| | EVA 763 | 27.3 µg/cm$^2$/day |
| | Polyethylene MA7800 | 4.6 µg/cm$^2$/day |
| Lambdacyhalothrin | polyurethane 3100 | 0.7 µg/cm$^2$/day |
| | polyurethane 2200 | 2.0 µg/cm$^2$/day |
| | EVA 763 | 20.6 µg/cm$^2$/day |
| | Polyethylene MA78000 | 5.2 µg/cm$^2$/day |
| Tefluthrin | polyurethane 3100 | 6.4 µg/cm$^2$/day |
| | polyurethane 2200 | 25.0 µg/cm$^2$/day |
| | EVA 763 | 40.4 µg/cm$^2$/day |
| | Polyethylene MA78000 | 27.0 µg/cm$^2$/day |
| Permethrin | polyurethane 3100 | 1.4 µg/cm$^2$/day |
| | polyurethane 2200 | 1.3 µg/cm$^2$/day |
| | EVA 763 | 28.5 µg/cm$^2$/day |
| | Polyethylene MA78000 | 4.0 µg/cm$^2$/day |

From the foregoing description one skilled in the art can easily ascertain the essential characteristics of this invention and without department from the spirit and scope of the invention thereof can make changes and modifications of the invention in order to adapt it to the various usages and conditions. It is intended that the scope of the invention be defined by the following claims including all equivalents.

What is claimed is:

1. A combination of a structure and a controlled release barrier, said combination comprising:
   a structure, said structure being free of crawling or soil borne insects; and
   a controlled release barrier, said barrier comprising
      78–98 weight percent of polymeric matrix having an outside surface;
      2–15 weight percent of pesticide, said pesticide being dispersed throughout said matrix; and
      0–7 weight percent of a carrier, said barrier being placed at all entry points for accessing the structure by crawling or soil borne insects so as to prevent intrusion of said structure by the crawling or soil borne insects, said pesticide releasing to the surface of the polymeric matrix at a rate of least about 10 µg/cm$^2$/day so as to repel or kill said crawling or soil borne insects coming in contact with the pesticide.

2. The structure of claim 1 wherein the polymeric matrix is selected from the group consisting of silicones, EVA, urethanes, polyurethanes, acrylonitrile, butadiene, acrylic rubber, isoprene, polyethylenes, and styrene-vinyl rubber.

3. The structure of claim 2 wherein the polymeric matrix further includes a carrier for controlling the release rate.

4. The structure of claim 3 wherein the carrier is selected from the group consisting of carbon black, clay and amorphous silica.

5. The structure of claim 4 wherein the carrier is carbon black.

6. The structure of claim 3 wherein the concentration of the carrier is from about 2 to about 7 percent of the total weight of the matrix.

7. The structure of claim 4 wherein the concentration of the carrier is from about 3 to about 5 percent of the total weight of the matrix.

8. The structure of claim 1 wherein the concentration of the pesticide is in the range from about 2 to about 15 percent of the total weight of the matrix.

9. The structure of claim 3 wherein the concentration of pesticide is from about 5 to about 10 percent of the total weight of the matrix.

10. The structure of claim 8 wherein the pesticide is deltamethrin.

11. The structure of claim 8 wherein the pesticide is cypermethrin.

12. The structure of claim 8 wherein the pesticide is lambdacyhalothrin.

13. The structure of claim 8 wherein the pesticide is tefluthrin.

14. The structure of claim 8 wherein the pesticide is permethrin.

15. The structure of claim 1 wherein the barrier is large enough to continue releasing the pesticide at a rate above 10 µg/cm$^2$/day for a time period from about 6 months to about 5 years.

16. A combination of a structure and a controlled release barrier, said combination comprising:
   a structure, said structure being free of cold-blooded vertebrae animals; and
   a controlled release barrier, said barrier comprising
      78–98 weight percent of polymeric matrix having an outside surface;

2–15 weight percent of pesticide, said pesticide being dispersed throughout said matrix; and 0–7 weight percent of a carrier, said barrier being placed at all entry points for accessing the structure by cold-blooded vertebrae animals so as to prevent intrusion of said structure by the cold-blooded vertebrae animals, said pesticide releasing to the surface of the polymeric matrix at a rate of least about 40 $\mu g/cm^2$/day so as to repel or kill cold-blooded vertebrae animals coming in contact with the pesticide.

17. The structure of claim 16 wherein the polymeric matrix is selected from the group consisting of silicones, EVA, urethanes, polyurethanes, acrylonitrile butadiene, acrylic rubber, isoprene, polyethylenes, and styrene-vinyl rubber.

18. The structure of claim 17 wherein the polymeric matrix further includes a carrier for controlling the release rate.

19. The structure of claim 18 wherein the carrier is selected from the group consisting of carbon black, clay and amorphous silica.

20. The structure of claim 19 wherein the carrier is carbon black.

21. The structure of claim 18 wherein the concentration of the carrier is from about 2 to about 7 percent of the total weight of the matrix.

22. The structure of claim 19 wherein the concentration of the carrier is from about 3 to about 5 percent of the total weight of the matrix.

23. The structure of claim 16 wherein the concentration of the pesticide is in the range from about 2 to about 15 percent of the total weight of the matrix.

24. The structure of claim 18 wherein the concentration of pesticide is from about 5 to about 10 percent of the total weight of the matrix.

25. The structure of claim 23 wherein the pesticide is deltamethrin.

26. The structure of claim 23 wherein the pesticide is cypermethrin.

27. The structure of claim 23 wherein the pesticide is lambdacyhalothrin.

28. The structure of claim 23 wherein the pesticide is tefluthrin.

29. The structure of claim 23 wherein the pesticide is permethrin.

30. The structure of claim 16 wherein the barrier is large enough to continue releasing the pesticide at a rate above 40 $\mu g/cm^2$/day for a time period from about 6 months to about 5 years.

31. The structure of claim 1, wherein the pesticide released to the surface of the polymeric matrix is absorbed by a permeable structure or object in contact with the barrier.

32. The structure of claim 1, wherein the pesticide released to the surface of the polymeric matrix is absorbed by a permeable structure or object in proximity to the barrier.

33. The structure of claim 1, wherein the pesticide is lambdacyhalothrin.

34. The structure of claim 33, wherein the pesticide releases at a rate between 0.7 $\mu g/cm^2$/day to 20.6 $\mu g/cm^2$/day.

35. The structure of claim 33, wherein the pesticide releases at a rate above 0.7 $\mu g/cm^2$/day.

36. The structure of claim 16, wherein the pesticide released to the surface of the polymeric matrix is absorbed by a permeable structure or object in contact with the barrier.

37. The structure of claim 16, wherein the pesticide released to the surface of the polymeric matrix is absorbed by a permeable structure or object in proximity to the barrier.

38. The structure of claim 16, wherein the pesticide is lambdacyhalothrin.

39. The structure of claim 38, wherein the pesticide releases at a rate between 0.7 $\mu g/cm^2$/day to 20.6 $\mu g/cm^2$/day.

40. The structure of claim 38, wherein the pesticide releases at a rate above 0.7 $\mu g/cm^2$/day.

41. A combination of a structure and a controlled release barrier, said combination comprising:

a structure, said structure being free of crawling or soil borne insects; and a controlled release barrier, said barrier comprising
78–98 weight percent of polymeric matrix having an outside surface;
2–15 weight percent of pesticide, said pesticide being dispersed throughout said matrix; and
0–7 weight percent of a carrier, said barrier being placed at all entry points for accessing the structure by crawling or soil borne insects so as to prevent intrusion of said structure by the crawling or soil borne insects, said pesticide releasing to the surface of the polymeric matrix at a rate so as to repel said crawling or soil borne insects coming in contact with the pesticide.

42. A combination of a structure and a controlled release barrier, said combination comprising:

a structure, said structure being free of cold-blooded vertebrae animals; and a controlled release barrier, said barrier comprising
78–98 weight percent of polymeric matrix having an outside surface;
2–15 weight percent of pesticide, said pesticide being dispersed throughout said matrix; and
0–7 weight percent of a carrier, said barrier being placed at all entry points for accessing the structure by cold-blooded vertebrae animals so as to prevent intrusion of said structure by the cold-blooded vertebrae animals, said pesticide releasing to the surface of the polymeric matrix at a rate so as to repel said cold-blooded vertebrae animals coming in contact with the pesticide.

43. The structure of claim 1, wherein the structure is an electrical power distribution system, a building, a plant nursery, a house, or a living area.

44. The structure of claim 16, wherein the structure is an electrical power distribution system, a building, a plant nursery, a house, or a living area.

45. The structure of claim 41, wherein the polymeric matrix is selected from the group consisting of silicones, EVA, urethanes, polyurethanes, acrylonitrile butadiene, acrylic rubber, isoprene, polyethylenes, and styrene-vinyl rubber.

46. The structure of claim 45, wherein the polymeric matrix further includes a carrier for controlling the release rate.

47. The structure of claim 46, wherein the carrier is selected from the group consisting of carbon black, clay and amorphous silica.

48. The structure of claim 47, wherein the carrier is carbon black.

49. The structure of claim 46, wherein the concentration of the carrier is from about 2 to about 7 percent of the total weight of the matrix.

50. The structure of claim 47, wherein the concentration of the carrier is from about 3 to about 5 percent of the total weight of the matrix.

51. The structure of claim 41, wherein the concentration of the pesticide is in the range from about 2 to about 15 percent of the total weight of the matrix.

52. The structure of claim 46, wherein the concentration of pesticide is from about 5 to about 10 percent of the total weight of the matrix.

53. The structure of claim 41, wherein the pesticide is selected from the group consisting of deltamethrin, cypermethrin, lambdacyhalothrin, tefluthrin, and permethrin.

54. The structure of claim 41, wherein the barrier is large enough to continue releasing the pesticide at a rate so as to repel the crawling or soil borne insects coming in contact with the pesticide for a time period from about 6 months to about 5 years.

55. The structure of claim 41, wherein the pesticide released to the surface of the polymeric matrix is absorbed by a permeable structure or object in contact with the barrier.

56. The structure of claim 41, wherein the pesticide released to the surface of the polymeric matrix is absorbed by a permeable structure or object in proximity to the barrier.

57. The structure of claim 41, wherein the pesticide is lambdacyhalothrin.

58. The structure of claim 42, wherein the polymeric matrix is selected from the group consisting of silicones, EVA, urethanes, polyurethanes, acrylonitrile butadiene, acrylic rubber, isoprene, polyethylenes, and styrene-vinyl rubber.

59. The structure of claim 58, wherein the polymeric matrix further includes a carrier for controlling the release rate.

60. The structure of claim 59, wherein the carrier is selected from the group consisting of carbon black, clay and amorphous silica.

61. The structure of claim 60, wherein the carrier is carbon black.

62. The structure of claim 59, wherein the concentration of the carrier is from about 2 to about 7 percent of the total weight of the matrix.

63. The structure of claim 60, wherein the concentration of the carrier is from about 3 to about 5 percent of the total weight of the matrix.

64. The structure of claim 42, wherein the concentration of the pesticide is in the range from about 2 to about 15 percent of the total weight of the matrix.

65. The structure of claim 59, wherein the concentration of pesticide is from about 5 to about 10 percent of the total weight of the matrix.

66. The structure of claim 42, wherein the pesticide is selected from the group consisting of deltamethrin, cypermethrin, lambdacyhalothrin, tefluthrin, and permethrin.

67. The structure of claim 42, wherein the barrier is large enough to continue releasing the pesticide at a rate so as to repel the crawling or soil borne insects coming in contact with the pesticide for a time period from about 6 months to about 5 years.

68. The structure of claim 42, wherein the pesticide released to the surface of the polymeric matrix is absorbed by a permeable structure or object in contact with the barrier.

69. The structure of claim 42, wherein the pesticide released to the surface of the polymeric matrix is absorbed by a permeable structure or object in proximity to the barrier.

70. The structure of claim 42, wherein the pesticide is lambdacyhalothrin.

* * * * *

UNITED STATES PATENT AND TRADEMARK OFFICE
CERTIFICATE OF CORRECTION

PATENT NO. : 6,331,308 B1
DATED : December 18, 2001
INVENTOR(S) : Van Voris et al.

It is certified that error appears in the above-identified patent and that said Letters Patent is hereby corrected as shown below:

<u>Title page,</u>
Item [63], Related U.S. Application Data, delete:

"which is a continuation-in-part of application No. 07/555,113, filed on July 19, 1990, now Pat. No. 4,998,959, which is a continuation-in-part of application No. 06/314,809, filed on Oct. 26, 1981, now abandoned, which is a continuation-in-part of application No. 06/314,810, filed on Oct. 26, 1981, now abandoned"

Signed and Sealed this

Fifth Day of November, 2002

*Attest:*

*Attesting Officer*

JAMES E. ROGAN
*Director of the United States Patent and Trademark Office*

UNITED STATES PATENT AND TRADEMARK OFFICE
Certificate

Patent No. 6,331,308 B1                                                                           Patented: December 18, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter Van Voris, Richland, WA (US); Dominic A. Cataldo, Kennewick, WA (US); Crystal J. Driver, Richmond, WA (US).

Signed and Sealed this Twenty-seventh Day of November 2007.

WILLIAM R. DIXON, JR.
*Supervisory Patent Examiner*
Art Unit 1600